US00PP11537P

United States Patent [19]

Sweet

[11] Patent Number: Plant 11,537

[45] Date of Patent: Oct. 3, 2000

[54] ST. AUGUSTINE GRASS PLANT NAMED 'DWARF #601'

[75] Inventor: Jack S. Sweet, St. Petersburg, Fla.

[73] Assignee: Pursley Distributing, Inc., Bradenton, Fla.

[21] Appl. No.: 09/108,756

[22] Filed: Jul. 2, 1998

[51] Int. Cl.[7] ..... A01H 5/00

[52] U.S. Cl. ..... Plt./392

[58] Field of Search ..... Plt./392, 384

[56] References Cited

U.S. PATENT DOCUMENTS

| | | | |
|---|---|---|---|
| P.P. 3,491 | 2/1974 | Garrett et al. | Plt./392 |
| P.P. 3,834 | 3/1976 | Garrett | Plt./392 |
| P.P. 4,097 | 9/1977 | Gruis et al. | Plt./392 |
| P.P. 9,395 | 12/1995 | Kirkland et al. | Plt./392 |

*Primary Examiner*—Howard J. Locker
*Assistant Examiner*—Wendy A Baker
*Attorney, Agent, or Firm*—Pettis & Van Royen, PA

[57] ABSTRACT

A new dwarf variety of St. Augustine grass (*Stenotapharum secundatum*) characterized by its flat, low growth habit and its deep green color.

6 Drawing Sheets

BACKGROUND OF THE INVENTION

The invention described herein is a new and distinct dwarf variety of St. Augustine grass (*Stenotaphrum secundatum*). I discovered this plant in a group of seedlings of unknown parentage, but which are believed to have resulted from the self-breeding of the patented variety 'Seville', U.S. Plant Pat. No. 4,097, also known as Pursley's Seville. The new variety was selected by me as a single variant plant from a crop of the parent variety being grown under my direction and control at my home in St. Petersburg, Fla. This new grass was observed by me to be a distinct, new dwarf type, with consistent fast growth and with a deeper green color than other known types of St. Augustine grass. I assigned to this new genotype the number 601 to identify it as I divided and expanded it as a new variety.

I proceeded to expand my new seedling by vegetative division using two or three node sections to produce new pots and trays of the 'Dwarf #601'. The new grass continued to thrive, proving to be truly a new dwarf, low growing type of St. Augustine grass not previously known. It consistently maintained low growth and short blades, with most of the blades extending laterally rather than upwardly as is common in most St. Augustine varieties. These traits are maintained when propagated asexually.

As indicated above, asexual reproduction of my new 'Dwarf #601' was performed by me by vegetative division in St. Petersburg, Fla., and in Manatee County, Fla.

As a varietal name for the new grass, I have chosen 'Dwarf #601'.

SUMMARY OF THE INVENTION

'Dwarf #601' is a distinctive, new dwarf variety of St. Augustine grass characterized by its low, spreading starburst-like growth habit and its dark green color. These traits are maintained when propagated asexually.

BRIEF DESCRIPTION OF THE ILLUSTRATIONS

Figure 3:
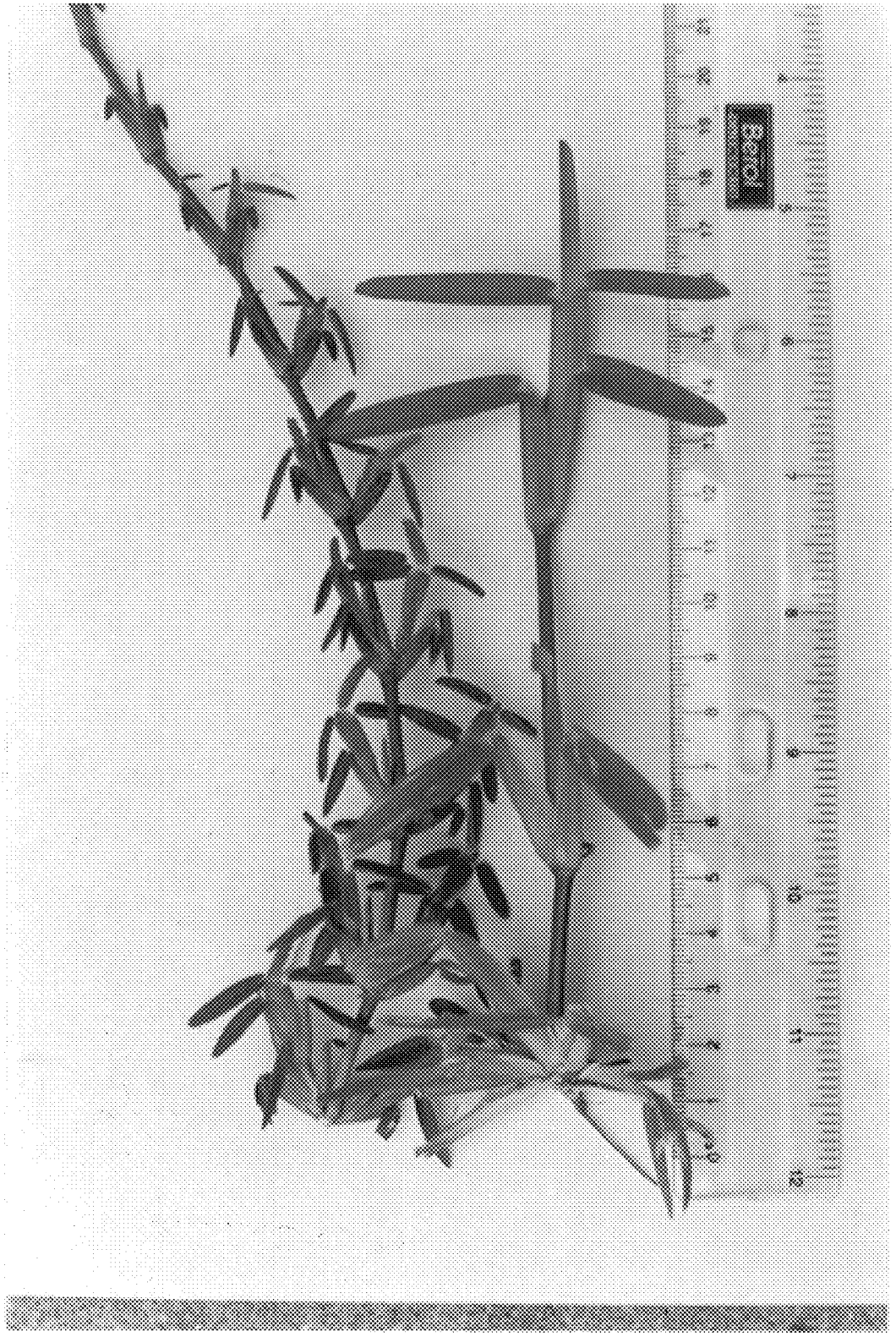

FIG. 3 provides a direct comparison of the grass of this invention on the left, and the parent grass on the right.

Figure 4:
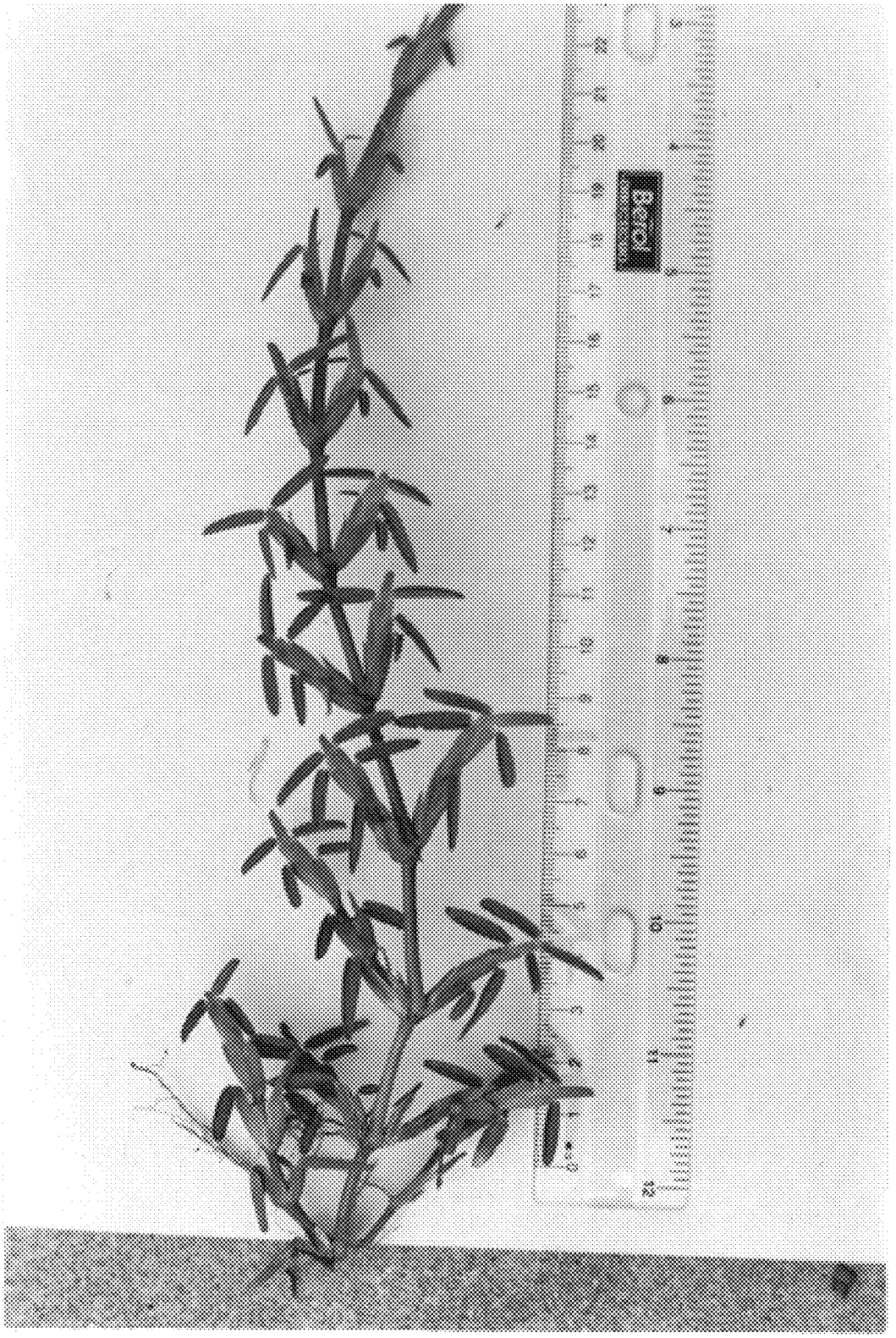

FIG. 4 illustrates the excellent branching characteristics of the grass of this invention.

Figure 5:
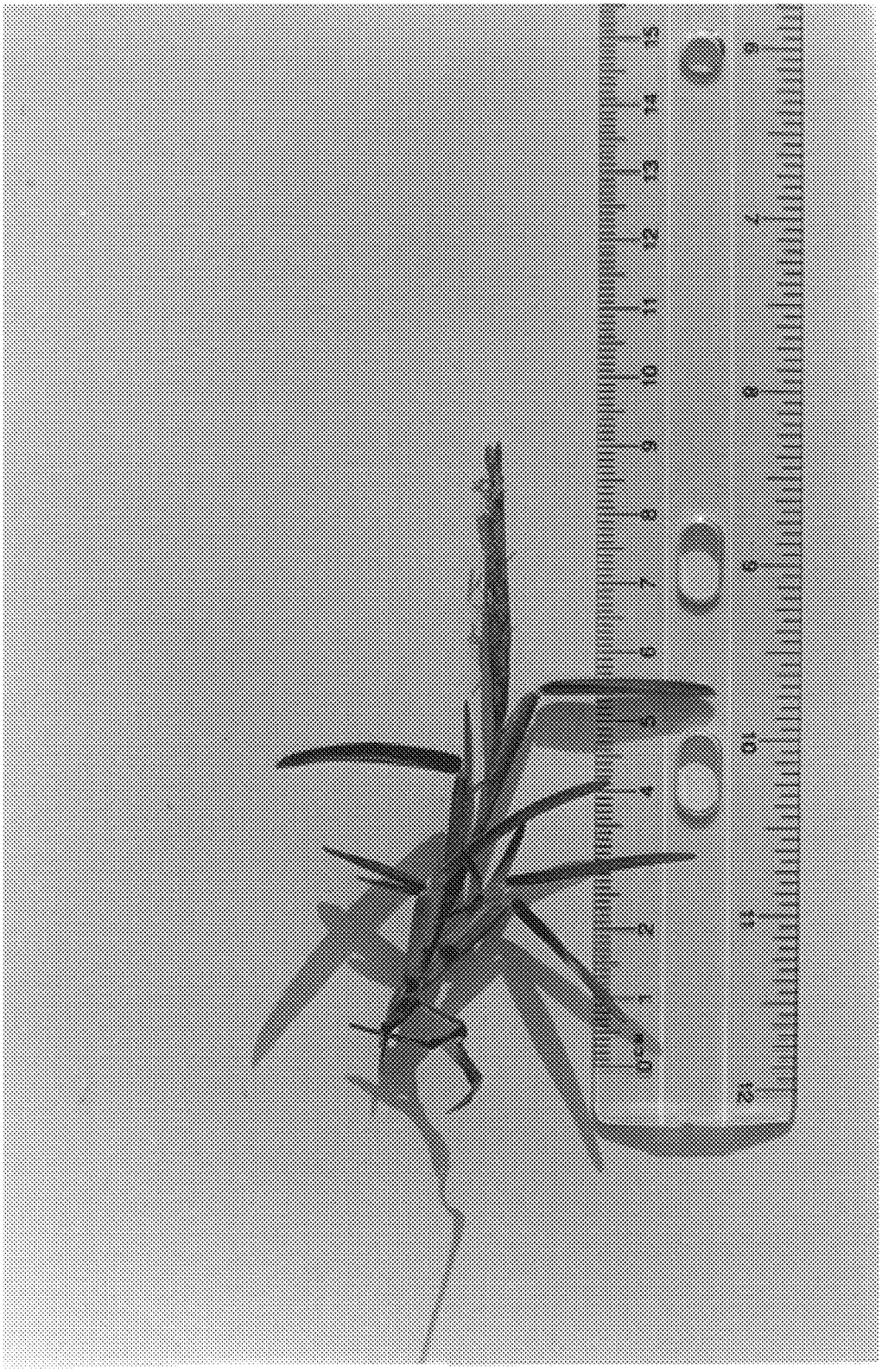

FIG. 5 illustrates an individual culm of the grass of this invention including the seed spike with anthers and pollen.

Figure 6:
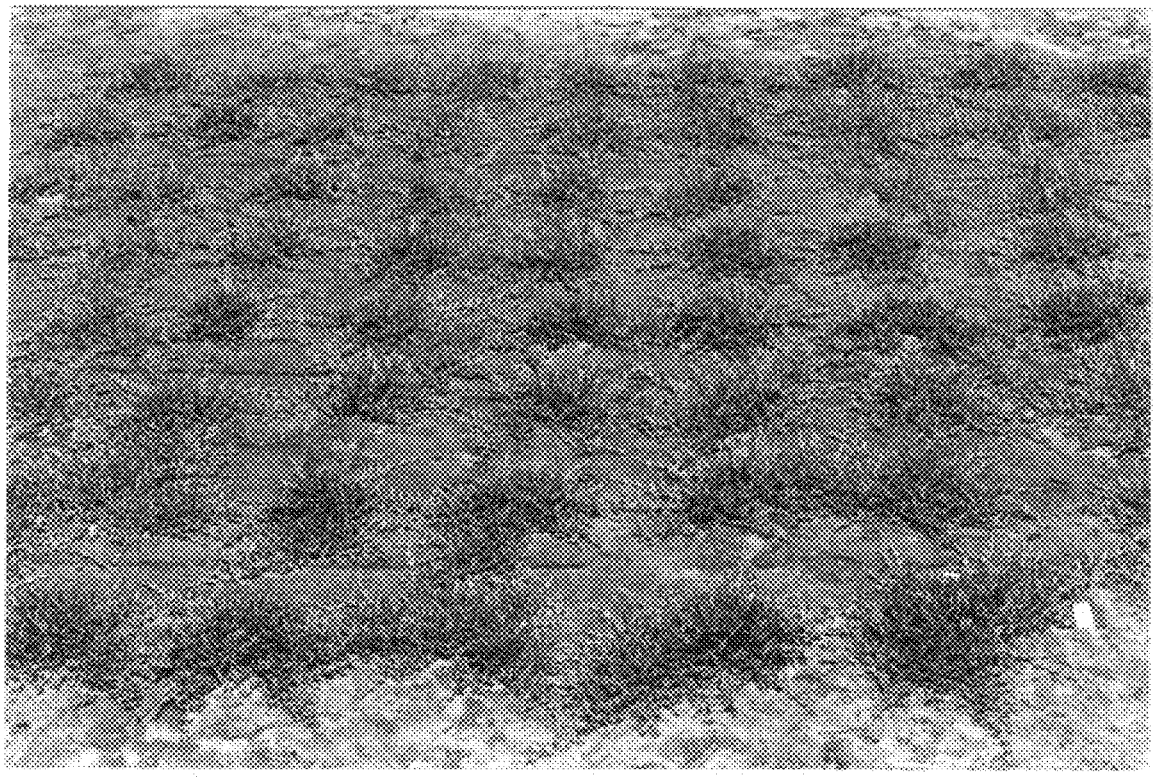

FIG. 6 illustrates the spreading characteristics of the grass of this invention from small plugs planted at twelve inch spacings.

DETAILED DESCRIPTION

The following is a detailed description of the new grass variety, based upon my observations of the plant as grown in field plots in Pinellas County and Manatee County, Fla. Color notations are based upon the Munsell color code.

'Dwarf #601' is a perennial vegetatively propagated St. Augustine grass (*Stenotaphrum secundatum*). It grows by creeping or ascendant stolons which root at the nodes. Its color is a deeper green color than other known varieties and is designated, according to the Munsell color chart, as dark yellowish green-10GY-4/5. For comparison, its parent 'Seville' color designation is olive green-7.5GY-4/4, according to the Munsell color chart. I have asexually propagated the new grass at locations in Florida by means of stolon cuttings containing one, two, three and more node sections. Planting stock has been grown, as shown in the illustrations, for use in studying performance and in comparing the 'Dwarf #601' to its parent.

Figure 1:
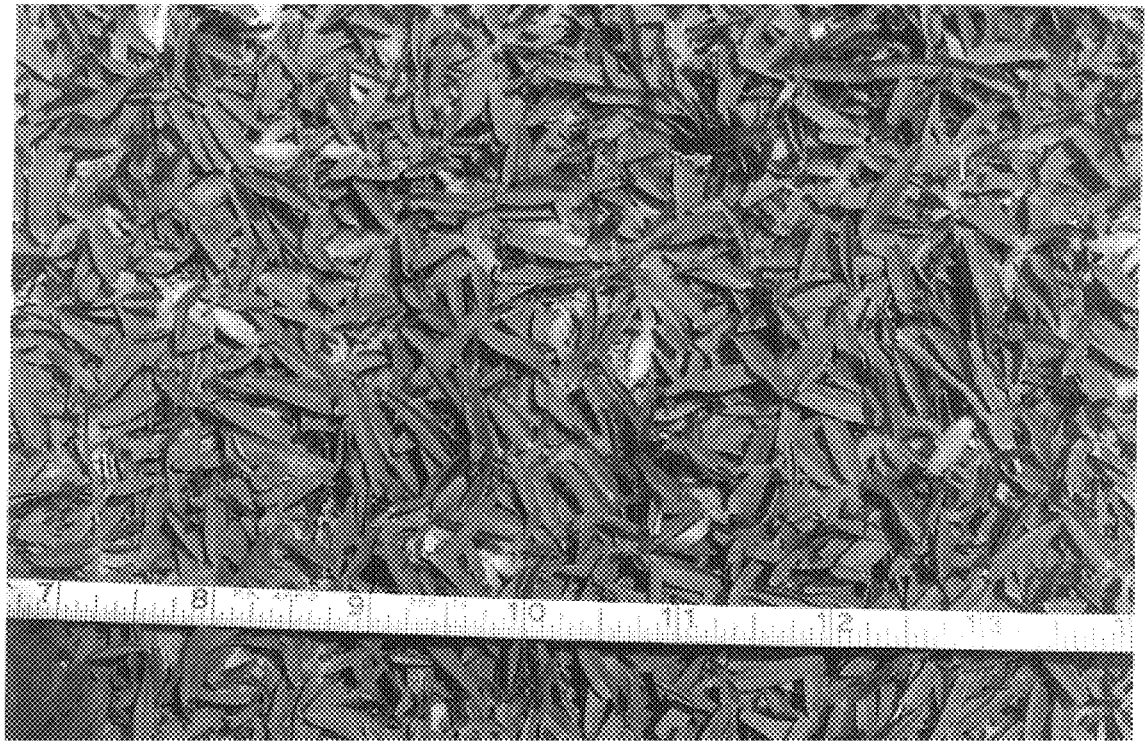
FIG. 1 shows the overall appearance of the grass of this invention.
Figure 2:
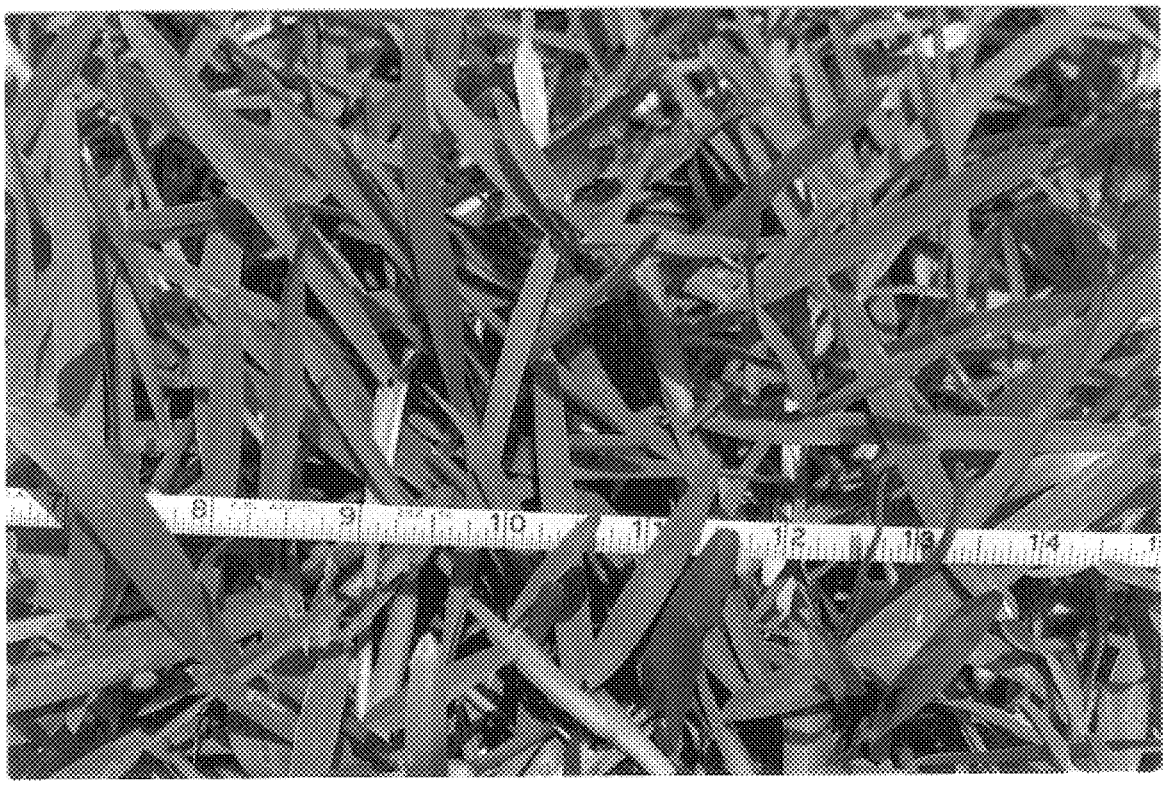
FIG. 2 shows a comparative appearance of the parent grass.

As clearly seen in the illustrations of FIGS. 1 and 6, this new grass variety thrives and is recognizable as a dwarf, low growing type of St. Augustine grass not previously known to be grown in the southern zone. 'Dwarf #601' consistently stays low and short-bladed with most of the blades extending laterally, instead of upwardly as do most varieties of St. Augustine.

The growth habit of 'Dwarf #601' is fast growing with multiple branching and many lateral shoots, the leaf blades tend to grow more parallel to the surface than other known varieties of St. Augustine, with little upright growth, except for the flowering culms which average in height about 7.4 cm, with a height range of about 5.5 cm to about 9.5 cm. Thus, the growth habit may be characterize as low stoleniferous. The flowering culms are primarily upright, sometimes branching, but most have only one raceme that averages about 58 mm.in length.

The internodes of 'Dwarf #601' are of a small, compressed ovate shape, flattened on the underneath side and approximately 2 mm×1.5 mm in size. The internodes average about 25 mm in length when grown in full sun. Also in full sun, the color of the internodes is green suffused with red. Referring to the Munsell color chart, the color designation is moderate olive brown-2.5Y.

Leaf blades are folded in bud, opening with a rounded tip. In full sun, the blades are about 4.5 mm wide, and average about 38 mm in length. The color of the leaf blade is dark yellowish green-10GY-4/5, according to the Munsell color chart. The leaf blades have longitudinal striations, but these striations are observed only with magnification.

The spikes average about 58 mm in length, and range from about 45 mm to about 85 mm, with a very fleshy, flattened rachis containing imbedded spikelets on one side of the terminal inflorescence. The long fleshy, flattened raceme average about 48 mm in length by about 3.5 mm in width. The spikelets are about 4 mm long, most of which produce viable seed.

The flower parts of the new variety include a stigma that is basically purple in color, and an anther that is basically creme/yellow on white filaments.

Size characteristics of the 'Dwarf #601' of this invention are compared with five other varieties of St. Augustine grass in Table #1, below.

TABLE 1

Comparative Leaf Blade Width, Leaf Blade Length and Internode Length

| Variety | Blade Width | Blade Length | Internode Length |
|---|---|---|---|
| 'Dwarf #601' | 4.5 mm | 38 mm | 20 mm |
| 'Seville' | 7.5 mm | 45 mm | 38.4 mm |
| 'Floratam' | 11.0 mm | 100 mm | 58.7 mm |
| 'Bitter Blue' | 9.3 mm | 94 mm | 37.2 mm |

TABLE 1-continued

Comparative Leaf Blade Width, Leaf Blade Length and Internode Length

| Variety | Blade Width | Blade Length | Internode Length |
|---|---|---|---|
| 'Palmetto' | 9.0 mm | 43 mm | 24.5 mm |
| 'Raleigh' | 7.4 mm | 46 mm | 45.3 mm |

My observation indicates that regular, weekly mowing of 'Dwarf #601' would not be necessary because of its flat, low growth characteristics. It furthermore appears to me that lawn production using 1½ to 2 inch plugs may even be superior to today's most common practice of planting new lawns with 3 inch plugs of standard St. Augustine varieties. This is a direct result of the excellent, starburst-like spreading characteristics of 'Dwarf #601', as clearly seen in the illustration of FIG. 6. Because of its dwarf habit, 'Dwarf #601' produces a dense, close-knit sod with many more branching nodes thann other know varieties of St. Augustine grass. I have also observed better shade tolerance with 'Dwarf #601' than its parent.

I have also observed than 'Dwarf #601' has extremely good resistance to grey leaf spot. During very moist, humid conditions when other St. Augustine varieties in my own test plots showed heavy gray leaf spot damage, 'Dwarf #601' showed little or no damage, suggesting that this new 'Dwarf #601' has a high resistance to natural fungus problems.

Finally, tests performed at the University of Florida in Gainesville, Fla., indicate that 'Dwarf #601' has a normal tolerance to atrazine, which is the principal chemical used on St. Augustine grasses as a weed control agent.

What is claimed is:

1. A new and distinct variety of St. Augustine grass, substantially as herein illustrated and described, characterized by its distinctive combination of vegetative characteristics, its dark green foliage, and its dwarf, spreading growth habit.

* * * * *